(12) United States Patent
Li et al.

(10) Patent No.: US 8,596,138 B2
(45) Date of Patent: Dec. 3, 2013

(54) DETECTING DEVICE

(75) Inventors: Chang-Jun Li, Wuhan (CN); Ming-Hui Luo, Wuhan (CN); Meng-Bin Yu, Wuhan (CN); Yu-Lin Liu, Wuhan (CN)

(73) Assignees: Hong Fu Jin Precision Industry (WuHan) Co., Ltd., Wuhan (CN); Hon Hai Precision Industry Co., Ltd., New Taipei (TW)

( * ) Notice: Subject to any disclaimer, the term of this patent is extended or adjusted under 35 U.S.C. 154(b) by 162 days.

(21) Appl. No.: 13/211,580

(22) Filed: Aug. 17, 2011

(65) Prior Publication Data

US 2012/0186360 A1 Jul. 26, 2012

(30) Foreign Application Priority Data

Jan. 26, 2011 (CN) .......................... 2011 1 0028267

(51) Int. Cl.
*G01N 3/22* (2006.01)
*G01N 3/02* (2006.01)

(52) U.S. Cl.
USPC ................................. 73/856; 73/857; 73/847

(58) Field of Classification Search
USPC ........................... 73/761, 847–854, 814, 856
See application file for complete search history.

(56) References Cited

U.S. PATENT DOCUMENTS

2012/0067141 A1* 3/2012 Chen et al. ................ 73/862.381
2012/0132016 A1* 5/2012 Chen et al. .................... 73/865.9

* cited by examiner

*Primary Examiner* — Lisa Caputo
*Assistant Examiner* — Jonathan Dunlap
(74) *Attorney, Agent, or Firm* — Altis & Wispro Law Group, Inc.

(57) ABSTRACT

A detecting device for performing fatigue tests on a pivoting piece includes a clamping module and an actuating module. The clamping module clamps the pivoting piece. The actuating module includes an elastic actuating shaft abutting the clamping module and a resilient member mounted in the elastic actuating shaft. The resilient member is adapted to push forward against spring pressure and retract by the release of spring tension so as to achieve cyclic movements in the pivoting piece.

20 Claims, 4 Drawing Sheets

DETECTING DEVICE

BACKGROUND

1. Technical Field

The present disclosure relates to detecting devices for performing fatigue tests.

2. Description of Related Art

Various types of tests are performed on electronic devices. One of the tests is used to perform fatigue tests on movable members of the electronic members. A typical fatigue test device includes an actuating tool which automatically and repeatedly presses buttons of the electronic devices. Then operators detect whether the buttons are worn out after being repeatedly used. However, such a fatigue test device can not perform fatigue tests to other movable members rather than the buttons, such as a pivotable plate.

Therefore, there is room for improvement within the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
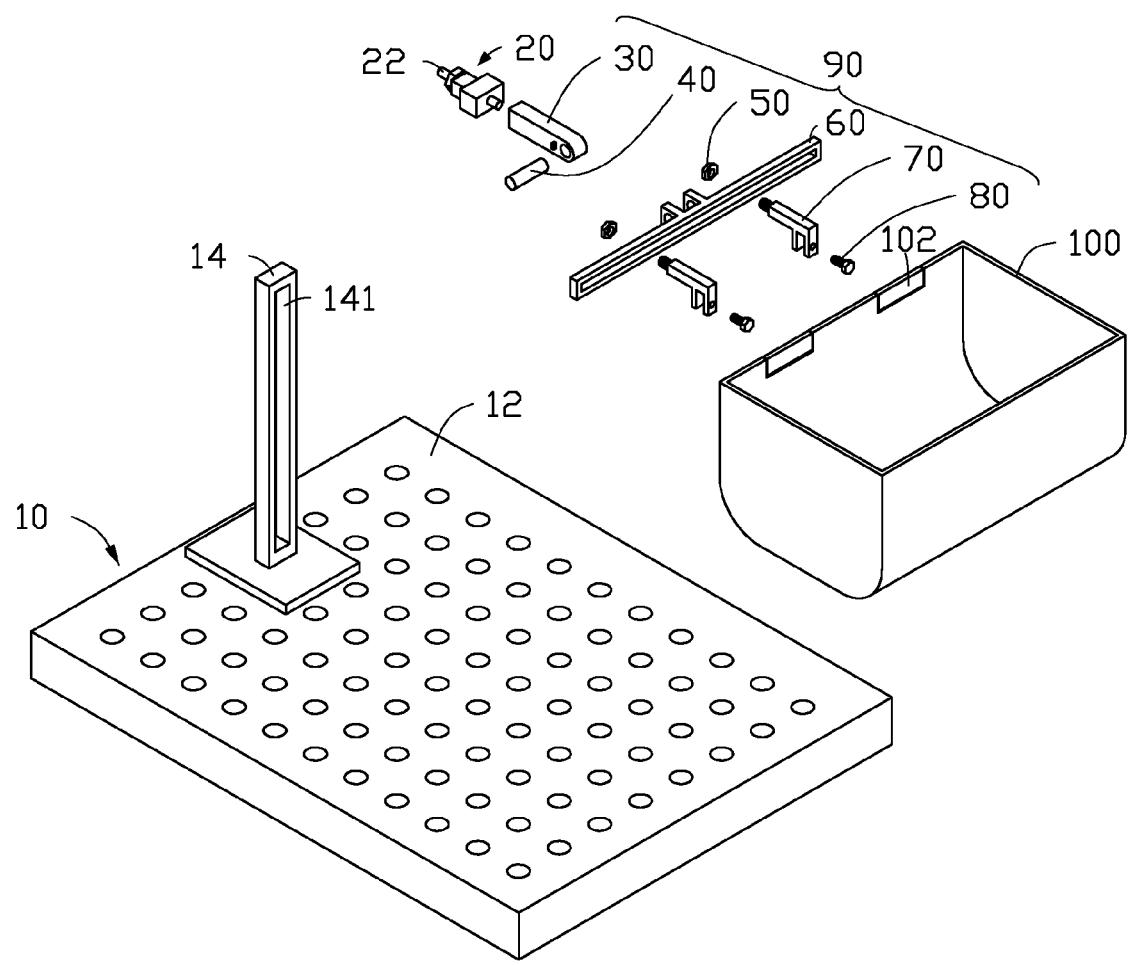
FIG. 1 is an exploded view of a detecting device according to an embodiment.
Figure 2:
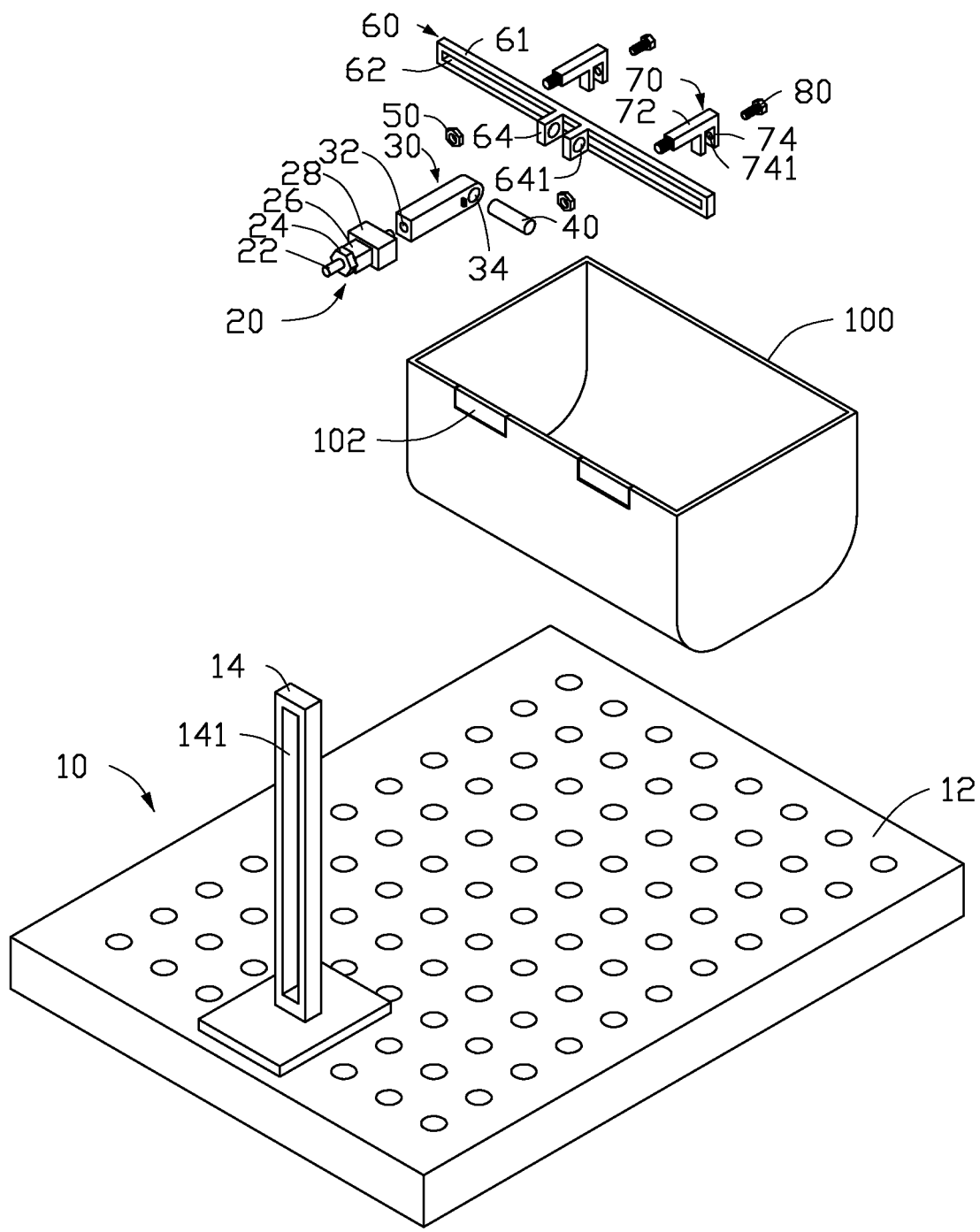
FIG. 2 is another exploded view of the detecting device of FIG. 1.

Referring to FIGS. 1 and 2, an embodiment of a detecting device includes a base module 10, an actuating module 20, and a clamping module 90. The detecting device is used to perform fatigue tests on a pair of pivotable pieces 102 of a shell 100. The clamping module 90 includes a connecting rod 30, a pivot shaft 40, a pair of nuts 50, a holder 60, a pair of clamping members 70, and a pair of fastening members 80.

The base module 10 includes a base panel 12 and a perpendicular support beam 14 attached to the base panel 12. A vertical slot 141 is defined in the support beam 14.

Referring to FIG. 2, the actuating module 20 includes an elastic actuating shaft 22, a securing member 24, a mounting block 26, and a holding block 28. The width of the mounting block 26 is substantially equal to the width of the vertical slot 141. The holding block 28 is wider than the mounting block 26. The mounting block 26 abuts the securing member 24 and the holding block 28 and is located between the securing member 24 and the holding block 28. The elastic actuating shaft 22 is partially received in the securing member 24, the mounting block 26, and the holding block 28. One end of the elastic actuating shaft 22 protrudes from the securing member 24, the other end protrudes from the holding block 28.

Figure 3:
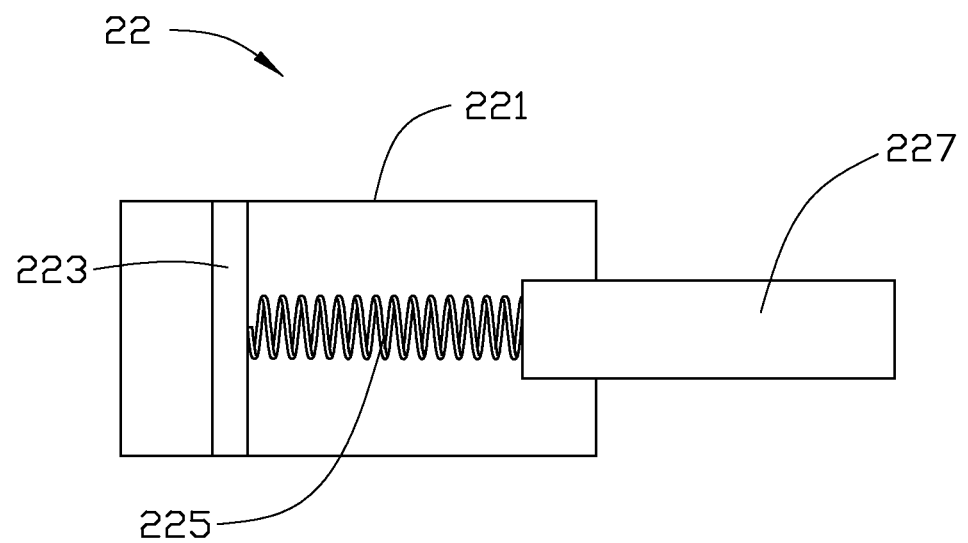
FIG. 3 illustrates the internal structure of an elastic actuating shaft of FIG. 2.

Referring to FIG. 3, in one embodiment, the elastic actuating shaft 22 includes a tubular case 221, a separation piece 223 movably mounted in the tubular case 221, a spring 225 mounted in the tubular case 221, and a movable post 227 connected to the spring 225. The spring 225 includes a first end attached to the separation piece 223 and a second end attached to the movable post 227. An air injection device (not shown) is utilized to actuate the elastic actuating shaft 22. The air injection device can rhythmically inject air into the tubular case 221. When the air pressure at a first side of the separation piece 223 exceeds the air pressure at the second side of the separation piece 223, the separation piece 223 moves the movable post 227 axially and compresses the spring 225. When the air injection device stops injecting air into the tubular case 221, the spring 225 resumes its original state and the movable post 227 moves back to its original position.

A mounting slot 32 is defined in a rear side of the connecting rod 30 for mounting the movable post 227. A pivot slot 34 is defined in a front side of the connecting rod 30 for mounting the pivot shaft 40. The mounting slot 32 is substantially perpendicular to the pivot slot 34. The holder 60 includes a rectangular main body 61 and a pair of parallel mounting pieces 64 extending from the rectangular main body 61. The distance between the pair of mounting pieces 64 is substantially equal to the thickness of the connecting rod 30. The thickness of the connecting rod 30 is substantially equal to the length of the pivot slot 34. A pivot hole 641 is defined in each of the pair of mounting pieces 64 corresponding to the pivot slot 34. A horizontal slot 62 is defined in the rectangular main body 61 for receiving the pair of clamping members 70. Each of the clamping members 70 includes a mounting rod 72 and a pair of clamping pieces 74 extending perpendicularly from the mounting rod 72. Each piece of the clamping pieces 74 is parallel to each other. The distance between the pair of clamping pieces 74 is substantially equal to the thickness of each of the pair of pivotable pieces 102. A securing hole 741 is defined in one of the pair of clamping pieces 74. The mounting rod 72 includes a threaded end whereby the rod 72 can be fixed to the holder 60.

Figure 4:
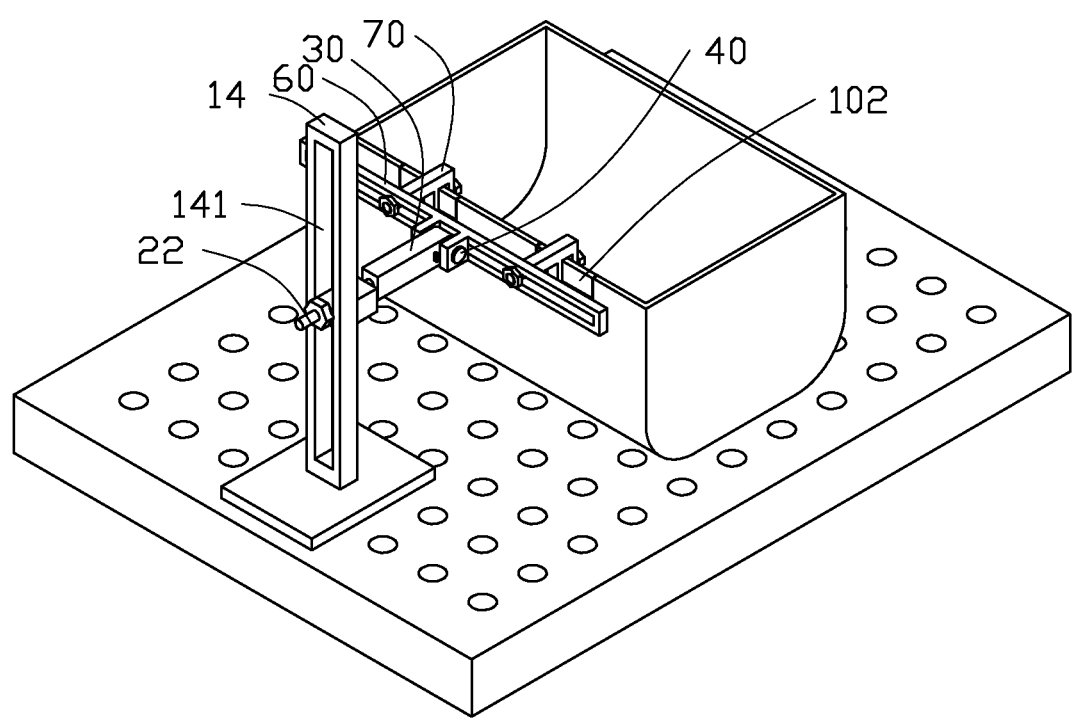
FIG. 4 is an assembled view of the detecting device of FIG. 1.

Referring to FIG. 4, in assembly, the front end of the connecting rod 30 is located between the pair of mounting pieces 64. The pivot holes 641 are aligned with the pivot slot 34. The pivot shaft 40 is engaged in the pivot holes 641 and the pivot slot 34, thereby pivotably attaching the connecting rod 30 to the holder 60. The threaded ends of the pair of clamping members 70 extend into and protrude from the horizontal slot 62 and are secured in place by the pair of nuts 50. The shell 100 is placed on the base panel 12. Each one of the pair of pivotable pieces 102 is clamped in one of the pieces of the clamping pieces 74. The pair of fastening members 80 in the securing holes 741 engage and hold the pieces 102 in place. The elastic actuating shaft 22 extends into the vertical slot 141. The mounting block 26 is engaged in the vertical slot 141. The holding block 28 abuts a first side of the support beam 14. The securing member 24 abuts a second side of the support beam 14. The actuating module 20 is secured to the support beam 14 at a desired height where the movable post 227 is aligned with the mounting slot 32. The movable post 227 is securely mounted in the mounting slot 32.

During the test, the air injection device injects air into the tubular case 221. The separation piece 223 is pushed axially. The spring 225 is compressed and pushes the movable post 227 and the connecting rod 30. The motion of the rod 30 causes the pivotable pieces 102 to rotate in relation to the shell 100. The connecting rod 30 is rotated slightly relative to the holder 60. Then the air injection device stops injection air into the tubular case 221. The spring 225 is released and resumes to its original state and the movable post 227 moves back to its original position. The connecting rod 30 moves together with the movable post 227. The holder 60 and the pair of clamping members 70 are pulled back by the connecting rod 30, thereby the pair of pivotable pieces 102 rotate back to their original positions. In this way, the pair of pivotable pieces 102 are repeatedly rotated back and forth for the desired period of time in order that the operators can determine whether the pair of pivotable pieces 102 pass the fatigue test.

In one embodiment, the actuating module 20 can use other resilient members to push the connecting rod 30.

While the present disclosure has been illustrated in detail in one or more embodiments, it is not intended to restrict or in any way limit the scope of the appended claims to such detail. Additional advantages and modifications within the spirit and scope of the present disclosure will readily appear to those skilled in the art, and the present disclosure is not to be limited to the specific details and illustrative examples shown and described.

What is claimed is:

1. A detecting device for performing a fatigue test on a pivotable piece comprising:
   an actuator;
   a clamping module for clamping the pivotable piece; and
   an actuating module comprising an elastic actuating shaft abutting the clamping module and a resilient member mounted in the elastic actuating shaft;
   wherein the resilient member biases the clamping module to drive the pivotable piece into rotation when the resilient member is pushed to be in a compressed state by the actuator, and biases the pivotable piece to rotate back to its original position after the resilient member is released.

2. The detecting device of claim 1, wherein the elastic actuating shaft comprises a tubular case, a separation piece slidably mounted in the tubular case, and a movable post, and the movable post comprises a first end mounted in the tubular case and a second end secured to the clamping module.

3. The detecting device of claim 2, wherein the resilient member is a spring, and the spring abuts the separation piece and the movable post and is located between the separation piece and the movable post.

4. The detecting device of claim 3, further comprising a base module, the base module comprises a base panel and a support beam substantially perpendicularly attached to the base panel, and the actuating module is attached to the support beam at a predetermined height.

5. The detecting device of claim 4, wherein a vertical slot is defined in the support beam, and the elastic actuating shaft is extended into the vertical slot along a horizontal direction and secured to the support beam.

6. The detecting device of claim 5, wherein the actuating module further comprises a mounting block engaged in the vertical slot, a securing member abutting a first side of the support beam, and a holding block attached to a second side of the support beam.

7. The detecting device of claim 1, wherein the clamping module comprises a holder, a connecting rod, and at least one clamping member securely attached to the holder; and the connecting rod comprises a first end secured to the elastic actuating shaft and a second end pivotably attached to the holder.

8. The detecting device of claim 7, wherein a mounting slot is defined in the connecting rod for mounting the elastic actuating shaft; a pivot slot is defined in the connecting rod and located opposite to the mounting slot; the holder comprises a main body and a pair of mounting pieces substantially perpendicularly extending from the main body; a pivot hole is defined in each of the pair of mounting pieces and aligned with the pivot slot; and a pivot shaft is engaged in the pivot hole and the pivot slot for pivotably attaching the connecting rod to the holder.

9. The detecting device of claim 8, wherein a horizontal slot is defined in the main body, and the at least one clamping member is mounted in the horizontal slot.

10. The detecting device of claim 9, wherein the at least one clamping member comprises a mounting rod and a pair of clamping pieces substantially perpendicularly extending from the mounting rod, and the mounting rod comprises a thread end engaged in the horizontal slot.

11. A detecting device for performing a fatigue test on a pivotable piece comprising:
    an actuator;
    a clamping module comprising a holder, a connecting rod pivotably attached to the holder, and at least one clamping member for clamping the pivotable piece; the at least one clamping member securely attached to the holder; and
    an actuating module, comprising an elastic actuating shaft mounted in the connecting rod, wherein the actuator drives the actuating module to cause the clamping module to move back and forth, thereby causing the pivotable piece to rotate back and forth correspondingly.

12. The detecting device of claim 11, wherein the actuating module further comprises a resilient member received in the elastic actuating shaft.

13. The detecting device of claim 12, wherein the elastic actuating shaft comprises a tubular case, a separation piece slidably mounted in the tubular case, and a movable post, and the movable post comprises a first end mounted in the tubular case and a second end secured to the clamping module.

14. The detecting device of claim 13, wherein the resilient member is a spring, and the spring abuts the separation piece and the movable post and is located between the separation piece and the movable post.

15. The detecting device of claim 14, further comprising a base module, the base module comprises a base panel and a support beam substantially perpendicularly attached to the base panel, and the actuating module is attached to the support beam at a desired height.

16. The detecting device of claim 15, wherein a vertical slot is defined in the support beam, and the elastic actuating shaft is extended into the vertical slot along a horizontal direction and secured to the support beam.

17. The detecting device of claim 16, wherein the actuating module further comprises a mounting block engaged in the vertical slot, a securing member abutting a first side of the support beam, and a holding block attached to a second side of the support beam.

18. The detecting device of claim 11, wherein a mounting slot is defined in the connecting rod for mounting the elastic actuating shaft; a pivot slot is defined in the connecting rod and located opposite to the mounting slot; the holder comprises a main body and a pair of mounting pieces substantially perpendicularly extending from the main body; a pivot hole is defined in each of the pair of mounting pieces and aligned with the pivot slot; and a pivot shaft is engaged in the pivot hole and the pivot slot for pivotably attaching the connecting rod to the holder.

19. The detecting device of claim 18, wherein a horizontal slot is defined in the main body, and the at least one clamping member is mounted in the horizontal slot.

20. The detecting device of claim 19, wherein the at least one clamping member comprises a mounting rod and a pair of clamping pieces substantially perpendicularly extending from the mounting rod, and the mounting rod comprises a thread end engaged in the horizontal slot.

* * * * *